US012620624B2

(12) United States Patent
Lee et al.

(10) Patent No.: US 12,620,624 B2
(45) Date of Patent: May 5, 2026

(54) NON-AQUEOUS ELECTROLYTIC SOLUTION FOR LITHIUM SECONDARY BATTERY AND LITHIUM SECONDARY BATTERY COMPRISING SAME

(71) Applicant: LG ENERGY SOLUTION, LTD., Seoul (KR)

(72) Inventors: Jeong-Beom Lee, Daejeon (KR); Ye-Eun Kim, Daejeon (KR); Seok-Koo Kim, Daejeon (KR); Je-Young Kim, Daejeon (KR)

(73) Assignee: LG ENERGY SOLUTION, LTD., Seoul (KR)

( * ) Notice: Subject to any disclaimer, the term of this patent is extended or adjusted under 35 U.S.C. 154(b) by 537 days.

(21) Appl. No.: 18/030,975

(22) PCT Filed: Nov. 30, 2021

(86) PCT No.: PCT/KR2021/017918
§ 371 (c)(1),
(2) Date: Apr. 7, 2023

(87) PCT Pub. No.: WO2022/114930
PCT Pub. Date: Jun. 2, 2022

(65) Prior Publication Data
US 2023/0411688 A1       Dec. 21, 2023

(30) Foreign Application Priority Data
Nov. 30, 2020     (KR) ........................ 10-2020-0165008

(51) Int. Cl.
| | |
|---|---|
| H01M 10/0567 | (2010.01) |
| C07C 309/06 | (2006.01) |
| C07C 309/65 | (2006.01) |
| H01M 10/0525 | (2010.01) |
| H01M 10/0568 | (2010.01) |
| H01M 10/0569 | (2010.01) |
| H01M 10/42 | (2006.01) |

(52) U.S. Cl.
CPC ....... H01M 10/0567 (2013.01); C07C 309/06 (2013.01); C07C 309/65 (2013.01); H01M 10/0525 (2013.01); H01M 10/0568 (2013.01); H01M 10/0569 (2013.01); H01M 10/4235 (2013.01); H01M 2300/0028 (2013.01); H01M 2300/0037 (2013.01)

(58) Field of Classification Search
None
See application file for complete search history.

(56) References Cited

U.S. PATENT DOCUMENTS

| | | |
|---|---|---|
| 2002/0039677 A1 | 4/2002 | Iwamoto et al. |
| 2010/0035146 A1 | 2/2010 | Fujii et al. |
| 2011/0111286 A1 | 5/2011 | Yamamoto et al. |
| 2014/0134501 A1 | 5/2014 | Li et al. |
| 2014/0287295 A1 | 9/2014 | Honda et al. |
| 2015/0064549 A1 | 3/2015 | Pinnell et al. |
| 2016/0164060 A1 | 6/2016 | Zhang et al. |
| 2018/0212276 A1 | 7/2018 | Liu et al. |
| 2019/0260080 A1 | 8/2019 | Jeong et al. |
| 2020/0099101 A1 | 3/2020 | Li et al. |
| 2020/0251780 A1 | 8/2020 | Park et al. |
| 2023/0246299 A1 | 8/2023 | Lee et al. |

FOREIGN PATENT DOCUMENTS

| | | |
|---|---|---|
| CN | 1333580 A | 1/2002 |
| CN | 101548425 A | 9/2009 |
| CN | 109546218 A | 3/2019 |
| CN | 110061176 A | 7/2019 |
| CN | 110854432 A | 2/2020 |
| EP | 3866244 A1 | 8/2021 |
| EP | 4142036 A1 | 3/2023 |
| JP | 2003346899 A  * | 12/2003 |
| JP | 2006-172950 A | 6/2006 |
| KR | 10-2011-0031414 A | 3/2011 |
| KR | 10-2015-0114460 A | 10/2015 |
| KR | 10-2016-0032632 A | 3/2016 |
| KR | 10-2016-0055084 A | 5/2016 |
| KR | 10-2018-0058633 A | 6/2018 |
| KR | 10-2020-0095860 A | 8/2020 |

OTHER PUBLICATIONS

English language machine translation of JP-2003346899-A. (Year: 2025).*
Li et al : "Ionic Liquids on the Basis of 2,3,4,6,7,8,9, 10-Octahydropyrimido[1,2-a]azepine (1,8-Diazabicyclo[5.4.0]undec-7-ene)", Russian Journal of Organic Chemistry, Jul. 1, 2006 (Jul. 1, 2006) pp. 1085-1091, XP093212127, Retrieved from the internet URL:        https://link.springer.com/article/10.1134/ S1070428006070256#preview*(p. 1071, paragraph bridging the two columns).

* cited by examiner

Primary Examiner — Eli S Mekhlin
(74) Attorney, Agent, or Firm — Bryan Cave Leighton Paisner LLP

(57)        ABSTRACT

An electrolyte for a lithium secondary battery including a wettability-improving additive having a trifluoromethyl-sulfonyl group. The electrolyte has reduced surface tension to improve the wettability of an electrode assembly with the electrolyte. Therefore, it is possible to ensure high electrolyte wettability even when the electrolyte includes a high-boiling point solvent or a high concentration of lithium salt.

5 Claims, No Drawings

NON-AQUEOUS ELECTROLYTIC SOLUTION FOR LITHIUM SECONDARY BATTERY AND LITHIUM SECONDARY BATTERY COMPRISING SAME

CROSS-REFERENCE TO RELATED APPLICATIONS

The present application is a US national phase of international Application No. PCT/KR2021/017918 filed on Nov. 30, 2021, and claims priority to Korean Patent Application No. 10-2020-0165008 filed on Nov. 30, 2020, the contents of which are incorporated for all purposes as if fully set forth herein.

TECHNICAL FIELD

The present disclosure relates to an electrolyte for a lithium secondary battery and a lithium secondary battery including the same.

BACKGROUND

As information society and personal IT devices and computer networks have been developed, and the overall social dependence on electric energy has increased, there is a need for developing technologies for storing and utilizing electric energy efficiently.

Among the technologies developed for the above-mentioned purpose, the most suitable technology for various uses is a secondary battery-based technology. In the case of a secondary battery, it can be downsized to such a degree that it may be applied to personal IT devices, and the like, and can also be applied to electric vehicles, electric power storage systems, and the like. Therefore, such secondary batteries have been spotlighted. Among the secondary battery technologies, lithium-ion batteries which are battery systems having, theoretically, the highest energy density have been given a lot of attention and have been applied to various devices.

A lithium-ion battery does not apply lithium metal directly to an electrode, but includes a positive electrode including a lithium-containing transition metal oxide, a negative electrode including a carbonaceous material, such as graphite, capable of storing lithium, an electrolyte functioning as a medium for conducting lithium ions, and a separator.

Among such components, the electrolyte has been known to affect the stability and safety of a battery significantly, and has been studied intensively.

The electrolyte for a lithium secondary battery includes a lithium salt, an organic solvent for dissolving the lithium salt, and functional additives, and the like. To improve the electrochemical properties of a battery, it is important to select such ingredients suitably. Typical lithium salts that are currently used include $LiPF_6$, $LiBF_4$, LiFSI (lithium fluorosulfonyl imide, $LiN(SO_2F)_2$), LiTFSI (lithium (bis)trifluoromethanesulfonyl imide, $LiN(SO_2CF_3)_2$), LiBOB (lithium bis(oxalate) borate, $LiB(C_2O_4)_2$), and the like. In addition, an ester-based organic solvent or an ether-based organic solvent is used as the organic solvent.

Recently, the use of an electrolyte containing a high concentration of lithium salt or a high-boiling point solvent having a boiling point of 150° C. or higher has been suggested to further improve the performance, particularly, heat resistance or electrochemical stability, of a lithium secondary battery. However, such an electrolyte material shows lower affinity to an electrode and lower affinity to a separator and has higher surface tension, as compared to a carbonate-based electrolyte mixed with 1.0-1.2 M of lithium salt, and thus is problematic in that it shows significantly low wettability to a polyolefin-based separator and an electrode using PVDF as a binder, that are generally used in lithium secondary batteries.

When the electrode/separator wettability is significantly low as mentioned above, activation processing time increases during a process for manufacturing a battery, and a high-temperature aging step is used to make the overall process complicated, resulting in an increase in the cost of the battery. In addition, the life characteristics and high-rate charging and output characteristics of a battery are affected adversely, which functions as an obstacle in applying such a novel electrolyte to commercialized batteries.

Thus, there is a need for developing a liquid electrolyte that does not degrade the wettability of an electrode assembly with an electrolyte when using a high concentration of lithium salt or an organic solvent, such as a high-boiling point solvent, as an ingredient of the electrolyte.

SUMMARY

The present disclosure is designed to solve the problems of the related art, and is directed to providing a liquid electrolyte capable of improving electrode wettability. The present disclosure is also directed to providing a lithium-ion secondary battery including the liquid electrolyte.

These and other objectives and advantages of the present disclosure may be understood from the following detailed description. Also, it will be easily understood that the objectives and advantages of the present disclosure may be realized by the embodiments of the appended claims and combinations thereof, but are not limited thereto.

According to a first embodiment of the present disclosure, there is provided a non-aqueous electrolyte for a secondary battery, including a lithium salt, an organic solvent and a wettability-improving additive, wherein the wettability-improving additive has a trifluoromethylsulfonyl group.

According to a second embodiment of the present disclosure, there is provided the non-aqueous electrolyte for a secondary battery as defined in the first embodiment, wherein the wettability-improving additive includes at least one of the compounds represented by Chemical Formula 1:

[Chemical Formula 1]

wherein R may be hydrogen (H) or a substituted or non-substituted C1-C10 alkyl group.

According to a third embodiment of the present disclosure, there is provided the non-aqueous electrolyte for a secondary battery as defined in the second embodiment, wherein R is a linear or branched alkyl, alkenyl or alkynyl group.

According to a fourth embodiment of the present disclosure, there is provided the non-aqueous electrolyte for a secondary battery as defined in the third embodiment, wherein at least one hydrogen atom of R is substituted with a halogen element selected from Cl, F, Br and I.

According to a fifth embodiment of the present disclosure, there is provided the non-aqueous electrolyte for a secondary battery as defined in any one of the first to the fourth embodiments, wherein the lithium salt includes $Li^+$, as a cation, and at least one selected from the group consisting of $F^-$, $Cl^-$, $Br^-$, $I^-$, $NO_3^-$, $N(CN)_2$, $BF_4^-$, $ClO_4^-$, $AlO_4^-$, $AlCl_4^-$, $PF_6^-$, $SbF_6^-$, $AsF_6^-$, $B_{10}Cl_{10}^-$, $BF_2C_2O_4^-$, $BC_4O_8^-$, $PF_4C_2O_4^-$, $PF_2C_4O_8^-$, $(CF_3)_2PF_4^-$, $(CF_3)_3PF_3^-$, $(CF_3)_4PF_2$, $(CF_3)_5PF^-$, $(CF_3)_6P^-$, $CF_3SO_3$, $C_4F_9SO_3$, $CF_3CF_2SO_3$, $(CF_3SO_2)_2N^-$, $(FSO_2)_2N^-$, $CF_3CF_2(CF_3)_2CO^-$, $(CF_3SO_2)_2$ $CH^-$, $CH_3SO_3^-$, $CF_3(CF_2)_7SO_3^-$, $CF_3CO_2^-$, $CH_3CO_2^-$, $PO_2F_2^-$, $SCN^-$ and $(CF_3CF_2SO_2)_2N^-$, as an anion.

According to a sixth embodiment of the present disclosure, there is provided the non-aqueous electrolyte for a secondary battery as defined in any one of the first to the fifth embodiments, wherein the additive represented by Chemical Formula 1 is used in an amount of 0.05 wt %-3 wt % based on 100 wt % of the non-aqueous electrolyte for a lithium-ion secondary battery.

According to a seventh embodiment of the present disclosure, there is provided the non-aqueous electrolyte for a secondary battery as defined in any one of the first to the sixth embodiments, wherein the organic solvent includes a nitrile-based organic solvent.

According to an eighth embodiment of the present disclosure, there is provided the non-aqueous electrolyte for a secondary battery as defined in the seventh embodiment, wherein the nitrile-based organic solvent includes succinonitrile, adiponitrile, acetonitrile, propionitrile, butyronitrile, glutaronitrile, pimelonitrile, suberonitrile, valeronitrile, caprylonitrile, heptane nitrile, cyclopentane carbonitrile, cyclohexane carbonitrile, 2-fluorobenzonitrile, 4-fluorobenzonitrile, difluorobenzonitrile, trifluorobenzonitrile, phenylacetonitrile, 2-fluorophenyl acetonitrile, 4-fluorophenylacetonitrile, or a combination of two or more of these nitrile-based organic solvents.

According to a ninth embodiment of the present disclosure, there is provided the non-aqueous electrolyte for a secondary battery as defined in any one of the first to the eighth embodiments, which includes the lithium salt at a concentration of 1.5 M or more.

According to a tenth embodiment of the present disclosure, there is provided a lithium secondary battery including a positive electrode, a negative electrode, a separator and a non-aqueous electrolyte, wherein the non-aqueous electrolyte is the same as defined in any one of the first to the ninth embodiments.

The electrolyte for a lithium-ion secondary battery according to the present disclosure includes a wettability-improving additive having a trifluoromethylsulfonyl group, and thus shows reduced surface tension to improve the wettability of an electrode assembly with the electrolyte. Therefore, it is possible to ensure high electrolyte wettability even in the case of an electrolyte using a high-boiling point solvent or a high concentration of lithium salt.

DETAILED DESCRIPTION

Hereinafter, preferred embodiments of the present disclosure will be described in detail.

Prior to the description, it should be understood that the terms used in the specification and the appended claims should not be construed as limited to general and dictionary meanings, but interpreted based on the meanings and concepts corresponding to technical aspects of the present disclosure on the basis of the principle that the inventor is allowed to define terms appropriately for the best explanation.

The present disclosure relates to a non-aqueous electrolyte for a lithium secondary battery and a lithium secondary battery including the same.

Non-Aqueous Electrolyte for Lithium Secondary Battery

Particularly, according to an embodiment of the present disclosure, there is provided a non-aqueous electrolyte for a lithium secondary battery, including a lithium salt, an organic solvent and an electrolyte wettability-improving additive.

(1) Electrolyte Wettability-Improving Additive

According to the present disclosure, the electrolyte wettability-improving additive may include a compound represented by Chemical Formula 1. Particularly, the additive may be any one of the compounds represented by Chemical Formula 1 or a combination of two or more of these compounds:

[Chemical Formula 1]

$$R\!\!-\!\!O\!-\!\!\overset{\displaystyle O}{\underset{\displaystyle O}{\overset{\|}{\underset{\|}{S}}}}\!\!-\!\!\overset{F}{\underset{F}{\diagup}}\!\!-\!\!F,$$

wherein R may be hydrogen (H) or a substituted or non-substituted $C_1$-$C_{10}$ alkyl group. According to an embodiment of the present disclosure, R may be a linear or branched alkyl, alkenyl or alkynyl group. Meanwhile, at least one hydrogen atom of R, when the R is an alkyl group may be substituted with a halogen element selected from Cl, F, Br and I. According to an embodiment of the present disclosure, the compound represented by Chemical Formula 1 may include 1H,1H,5H-octafluoropentyl trifluoromethanesulfonate.

According to an embodiment of the present disclosure, the compound represented by Chemical Formula 1 may be used in an amount of 0.05 wt %-3 wt %, particularly 0.1 wt %-1 wt %, and more particularly 0.1 wt %-0.5 wt %, based on the total weight of the non-aqueous electrolyte.

When the compound represented by Chemical Formula 1 (i.e. additive) is used within the above-defined ranges, it is possible to obtain a secondary battery having improved overall performance. Particularly, R and the trifluoromethylsulfonyl group in the compound represented by Chemical Formula 1 may function as a surfactant showing nonpolarity and polarity, respectively, and thus can reduce the surface tension of the electrolyte, resulting in improved wettability of a separator and an electrode. For example, when the content of the compound represented by Chemical Formula 1 is less than 0.1 wt %, it is difficult to realize a desired improvement of the wettability. On the other hand, when the content of the compound represented by Chemical Formula 1 is more than 3 wt %, side reactions and byproducts are generated due to the excessive amount of additive to cause an increase in the resistance of a secondary battery during high-temperature storage.

Therefore, when the content of the compound represented by Chemical Formula 1 is 0.1 wt %-3 wt %, particularly 0.1-1 wt %, and more particularly 0.3-0.5 wt %, it is possible to improve electrolyte wettability, while inhibiting shortcomings such as side reactions, degradation of capacity and increased resistance, caused by the additive, to a highest degree.

(2) Lithium Salt

In the non-aqueous electrolyte for a lithium secondary battery according to an embodiment of the present disclosure, the lithium salt may be any lithium salt used conventionally for preparing an electrolyte for a lithium secondary battery with no particular limitation. For example, the lithium salt includes $Li^+$, as a cation, and at least one selected from the group consisting of $F^-$, $Cl^-$, $Br^-$, $I^-$, $NO_3^-$, $N(CN)_2^-$, $BF_4^-$, $ClO_4^-$, $AlO_4^-$, $AlCl_4^-$, $PF_6^-$, $SbF_6^-$, $AsF_6^-$, $B_{10}Cl_{10}^-$, $BF_2C_2O_4^-$, $BC_4O_8^-$, $PF_4C_2O_4^-$, $PF_2C_4O_8^-$, $(CF_3)_2PF_4^-$, $(CF_3)_3PF_3^-$, $(CF_3)_4PF_2$, $(CF_3)_5PF^-$, $(CF_3)_6P^-$, $CF_3SO_3^-$, $C_4F_9SO_3^-$, $CF_3CF_2SO_3^-$, $(CF_3SO_2)_2N^-$, $(FSO_2)_2N^-$, $CF_3CF_2(CF_3)_2CO^-$, $(CF_3SO_2)_2CH^-$, $CH_3SO_3^-$, $CF_3(CF_2)_7SO_3^-$, $CF_3CO_2^-$, $CH_3CO_2^-$, $PO_2F_2$, $SCN^-$ and $(CF_3CF_2SO_2)_2N^-$, as an anion. Particularly, the lithium salt may be at least one selected from the group consisting of LiCl, LiBr, LiI, $LiBF_4$, $LiClO_4$, $LiAlO_4$, $LiAlCl_4$, $LiPF_6$, $LiSbF_6$, $LiAsF_6$, $LiPO_2F_2$, $LiB_{10}Cl_{10}$, LiBOB ($LiB(C_2O_4)_2$), $LiCF_3SO_3$, LiTFSI ($LiN(SO_2CF_3)_2$), LiFSI ($LiN(SO_2F)_2$), $LiCH_3SO_3$, $LiCF_3CO_2$, $LiCH_3CO_2$, lithium difluoro(oxalate)borate (LiDFOB) and LiBETI ($LiN(SO_2CF_2CF_3)_2$), or a mixture of two or more lithium salts.

Meanwhile, according to an embodiment of the present disclosure, the lithium salt may include an imide-based lithium salt, such as LiFSi or LiTFSI. When such lithium salts are used at a high concentration, they cause an increase in viscosity of an electrolyte, which is not favorable to the wettability of an electrode or separator with the electrolyte. However, when the electrolyte wettability-improving additive is incorporated according to the present disclosure, it is possible to prevent degradation of electrolyte wettability and prevent degradation of electrochemical properties caused thereby, even when a high content of imide-based lithium salt is used.

According to an embodiment of the present disclosure, the lithium salt may be used at a concentration of 0.8 M-4.0 M. For example, the lithium salt may be used at a concentration of 1.0 M or more, 1.5 M or more, or 2.0 M or more. According to an embodiment of the present disclosure, the non-aqueous electrolyte includes the additive of Chemical Formula 1 and a lithium salt, wherein the lithium salt is used at a concentration of 1.5 M or more, or 2.0 M or more.

When the lithium salt is used at a concentration of less than 0.8 M, it is not possible to sufficiently improve the low-temperature output of a lithium secondary battery and improve the cycle characteristics of a lithium secondary battery during high-temperature storage. Meanwhile, a higher concentration of lithium salt may provide higher viscosity to cause degradation of electrolyte wettability for a liquid electrolyte.

However, because the electrolyte according to the present disclosure includes the electrolyte wettability-improving additive to reduce the surface tension thereof, it is possible to prevent the above-mentioned degradation of wettability and degradation of electrochemical properties caused thereby in the case of an electrolyte containing a high concentration of lithium salt.

(3) Organic Solvent

In the non-aqueous electrolyte for a lithium secondary battery according to the present disclosure, the organic solvent may include at least one selected from a nitrile-based organic solvent, a cyclic carbonate-based organic solvent, a linear carbonate-based organic solvent and an ester-based organic solvent.

The nitrile-based organic solvent may include succinonitrile, adiponitrile, acetonitrile, propionitrile, butyronitrile, glutaronitrile, pimelonitrile, suberonitrile, valeronitrile, caprylonitrile, heptane nitrile, cyclopentane carbonitrile, cyclohexane carbonitrile, 2-fluorobenzonitrile, 4-fluorobenzonitrile, difluorobenzonitrile, trifluorobenzonitrile, phenylacetonitrile, 2-fluorophenyl acetonitrile, 4-fluorophenylacetonitrile, or a combination thereof.

According to an embodiment of the present disclosure, the non-aqueous electrolyte may include the nitrile-based organic solvent and the additive, wherein the nitrile-based organic solvent may be used in an amount of 30 wt %-100 wt % based on 100 wt % of the organic solvent. For example, the nitrile-based organic solvent may be used in an amount of 50 wt % or more, 80 wt % or more, or 95 wt % or more. The nitrile-based organic solvent has a high boiling point, and thus improves the heat resistance and safety of the electrolyte. However, as the content of the nitrile-based organic solvent is increased, the surface tension of the non-aqueous electrolyte is increased to cause degradation of the wettability with the non-aqueous electrolyte. To solve the problem, the additive is used according to the present disclosure. When the non-aqueous electrolyte includes the nitrile-based organic solvent and the additive, it is possible to ensure the heat resistance and safety of a battery, while maintaining the surface tension of the electrolyte and electrolyte wettability at an adequate level.

The cyclic carbonate-based organic solvent is a high-viscosity organic solvent and an organic solvent having a high dielectric constant and capable of dissociating the lithium salt easily in the electrolyte. Particular examples of the cyclic carbonate-based organic solvent may include at least one organic solvent selected from the group consisting of ethylene carbonate (EC), propylene carbonate (PC), 1,2-butylene carbonate, 2,3-butylene carbonate, 1,2-pentylene carbonate, 2,3-pentylene carbonate and vinylene carbonate. Particularly, the cyclic carbonate-based organic solvent may include ethylene carbonate.

In addition, the linear carbonate-based organic solvent is an organic solvent having low viscosity and a low dielectric constant, and typical examples thereof may include at least one organic solvent selected from the group consisting of dimethyl carbonate (DMC), diethyl carbonate (DEC), dipropyl carbonate, ethyl methyl carbonate (EMC), methyl propyl carbonate and ethyl propyl carbonate. Particularly, the linear carbonate-based organic solvent may include ethyl methyl carbonate (EMC).

Meanwhile, according to an embodiment of the present disclosure, the cyclic carbonate and the linear carbonate may include a fluorinated carbonate in which at least one hydrogen atom is substituted with a fluorine atom. For example, the fluorinated carbonate may include trifluoroethylmethyl carbonate.

The ester-based organic solvent may include a linear ester-based organic solvent and/or a cyclic ester-based organic solvent. Particular examples of the linear ester-based organic solvent may include at least one organic solvent selected from the group consisting of methyl acetate, ethyl acetate, propyl acetate, methyl propionate, ethyl propionate, propyl propionate and butyl propionate. Such linear ester-based organic solvents can improve the ion conductivity of the electrolyte. In addition, the cyclic ester-based organic solvent may include at least one organic solvent selected from the group consisting of γ-butyrolactone, γ-valerolactone, γ-caprolactone, σ-valerolactone and ε-caprolactone.

Meanwhile, if necessary, the organic solvent may further include any organic solvent used conventionally for an electrolyte for a lithium secondary battery with no particular limitation. For example, the organic solvent may further include at least one organic solvent selected from ether-based organic solvents and amide-based organic solvents.

(4) Supplementary Additives

In addition, the non-aqueous electrolyte for a lithium secondary battery according to the present disclosure may further include supplementary additives, if necessary, to prevent decomposition of the non-aqueous electrolyte and a collapse of the negative electrode under a high-output environment, or to improve low-temperature high-rate discharge characteristics, high-temperature stability, overcharge-preventing effect, battery swelling-inhibiting effect at high temperature, and the like.

Typical examples of such supplementary additives may include at least one supplementary additive selected from the group consisting of cyclic carbonate-based compounds, halogen-substituted carbonate-based compounds, sultone-based compounds, sulfate-based compounds, phosphate-based compounds, borate-based compounds, benzene-based compounds, amine-based compounds, silane-based compounds and lithium salt-based compounds.

The cyclic carbonate-based compounds may include vinylene carbonate (VC) or vinylethylene carbonate. The halogen-substituted carbonate-based compounds may include fluoroethylene carbonate (FEC).

The sulfone-based compounds may include at least one compound selected from the group consisting of 1,3-propane sultone (PS), 1,4-butane sulfone, ethene sultone, 1,3-propene sultone (PRS), 1,4-butene sultone and 1-methyl-1,3-propene sultone.

The sulfate-based compounds may include ethylene sulfate (ESA), trimethylene sulfate (TMS), or methyl trimethylene sulfate (MTMS).

The phosphate-based compounds may include at least one compound selected from the group consisting of lithium difluoro(bisoxalato)phosphate, lithium difluorophosphate, tetramethyl trimethylsilyl phosphate, trimethylsilyl phosphite, tris(2,2,2-trifluoroethyl) phosphate and tris(trifluoroethyl) phosphite.

The borate-based compounds may include tetraphenyl borate and lithium oxalyl difluoroborate.

The benzene-based compounds may include fluorobenzene, the amine-based compounds may include triethanolamine or ethylenediamine, and the silane-based compounds may include tetravinylsilane.

The lithium salt-based compounds may include compounds different from the lithium salt contained in the non-aqueous electrolyte, and particularly, at least one compound selected from the group consisting of $LiPO_2F_2$, LiODFB, LiBOB (lithium bisoxalatoborate ($LiB(C_2O_4)_2$) and $LiBF_4$.

When the non-aqueous electrolyte for a lithium secondary battery includes vinylene carbonate, vinylethylene carbonate or succinonitrile, among the supplementary additives, it is possible to form a more rigid solid electrolyte interphase (SEI) film on the surface of the negative electrode during the initial activation of a secondary battery.

When using $LiBF_4$, it is possible to inhibit generation of gases caused by decomposition of the electrolyte during high-temperature storage, and thereby improve the high-temperature stability of a secondary battery.

Meanwhile, two or more of the supplementary additives may be used in combination, and the content of the supplementary additives may be 0.01 wt %-50 wt %, particularly 0.01 wt %-20 wt %, based on the total weight of the non-aqueous electrolyte. When the content of the supplementary additives is less than 0.01 wt %, it is not possible to sufficiently improve the low-temperature output, high-temperature storage characteristics and high-temperature life characteristics of a battery. When the content of the supplementary additives is larger than 50 wt %, excessive side reactions may occur during charging/discharging of a battery due to an excessive amount of additives. Particularly, when the additives for forming an SEI film are added in an excessive amount, they cannot be decomposed sufficiently at high temperature, resulting in formation of unreacted materials in the electrolyte at room temperature, or precipitation thereof. In this case, side-reactions may occur to cause degradation of the life or resistance characteristics of a secondary battery.

Lithium Secondary Battery

In another aspect of the present disclosure, there is provided a lithium secondary battery including the non-aqueous electrolyte for a lithium secondary battery according to the present disclosure.

Meanwhile, the lithium secondary battery according to the present disclosure may be obtained by forming an electrode assembly including a positive electrode, a negative electrode and a separator interposed between the positive electrode and the negative electrode, stacked successively therein, introducing the electrode assembly to a battery casing, and injecting the non-aqueous electrolyte according to the present disclosure.

The method for manufacturing the lithium secondary battery according to the present disclosure may be any method known to those skilled in the art, and a particular embodiment of the method will be explained hereinafter.

(1) Positive Electrode

The positive electrode may be obtained by coating a positive electrode slurry including a positive electrode active material, a binder, a conductive material and a solvent onto a positive electrode current collector, followed by drying and pressing.

The positive electrode current collector is not particularly limited, as long as it causes no chemical change in the corresponding battery and has conductivity. Particular examples of the positive electrode current collector may include stainless steel, aluminum, nickel, titanium, baked carbon, copper or stainless steel surface-treated with carbon, nickel, titanium or silver, and the like.

The positive electrode active material is a compound capable of reversible lithium intercalation/deintercalation, and particular examples thereof include lithium composite metal oxides containing lithium and at least one metal, such as cobalt, manganese, nickel or aluminum. More particularly, the lithium composite metal oxides may include lithium-manganese oxides (e.g. $LiMnO_2$, $LiMn_2O_4$, etc.), lithium-cobalt oxides (e.g., $LiCoO_2$, etc.), lithium-nickel oxides (e.g., $LiNiO_2$, etc.), lithium-nickel-manganese oxides (e.g., $LiNi_{1-Y}Mn_YO_2$ (wherein $0<Y<1$), $LiMn_{2-z}Ni_zO_4$ (wherein $0<Z<2$)), lithium-nickel-cobalt oxides (e.g., $LiNi_{1-Y1}Co_{Y1}O_2$ (wherein $0<Y1<1$)), lithium-manganese-cobalt oxides (e.g., $LiCo_{1-Y2}Mn_{Y2}O_2$ (wherein $0<Y2<1$), $LiMn_{2-z1}Co_{z1}O_4$ (wherein $0<Z1<2$)), lithium-nickel-manganese-cobalt oxides (e.g., $Li(Ni_pCo_qMn_{r1})O_2$ ($0<p<1$, $0<q<1$, $0<r1<1$, $p+q+r1=1$) or $Li(Ni_{p1}Co_{q1}Mn_{r2})O_4$ ($0<p1<2$, $0<q1<2$, $0<r2<2$, $p1+q1+r2=2$)), lithium-nickel-cobalt-transition metal (M) oxides (e.g., $Li(Ni_{p2}Co_{q2}Mn_{r3}MS_2)O_2$ (wherein M is selected from the group consisting of Al, Fe, V, Cr, Ti, Ta, Mg and Mo, and each of p2, q2, r3 and s2 represents the atomic proportion of each element satisfying $0<p2<1$, $0<q2<1$, $0<r3<1$, $0<s2<1$, and $p2+q2+r3+s2=1$)), and the like, and any one or more lithium composite metal oxides may be used. Particularly, the lithium composite metal oxides may include $LiCoO_2$, $LiMnO_2$, $LiNiO_2$, lithium nickel manganese cobalt oxides (e.g. $Li(Ni_{0.6}Mn_{0.2}Co_{0.2})O_2$, $Li(Ni_{0.5}Mn_{0.3}Co_{0.2})O_2$, $Li(Ni_{0.5}Mn_{0.1}Co_{0.1})O_2$, and the like), or lithium nickel cobalt aluminum oxides (e.g., $Li(Ni_{0.5}Co_{0.15}Al_{0.05})O_2$, etc.) with a view to improve the capacity characteristics and stability of a battery. In addition, considering the significance of the improvement depending on the types of the constitutional elements forming the lithium composite metal oxides and the mixing ratios thereof, the lithium composite metal oxides may include $Li(Ni_{0.6}Mn_{0.2}Co_{0.2})O_2$, $Li(Ni_{0.5}Mn_{0.3}Co_{0.2})O_2$, $Li(Ni_{0.7}Mn_{0.15}Co_{0.15})O_2$, $Li(Ni_{0.5}Mn_{0.1}Co_{0.1})O_2$, and the like, and any one or more lithium composite metal oxides may be used.

The positive electrode active material may be used in an amount of 80 wt %-99 wt %, particularly 90 wt %-99 wt %, based on the total weight of the solid content in the positive electrode slurry. When the positive electrode active material is used in an amount of 80 wt % or less, energy density decreases to cause degradation of capacity.

The binder is an ingredient which assists binding between an active material and a conductive material and binding to a current collector. In general, the binder may be added in an amount of 1 wt %-30 wt % based on the total weight of the solid content in the positive electrode slurry. Particular examples of the binder include polyvinylidene fluoride, polyvinyl alcohol, carboxymethyl cellulose (CMC), starch, hydroxypropyl cellulose, regenerated cellulose, polyvinyl pyrrolidone, tetrafluoroethylene, polyethylene, polypropylene, ethylene-propylene-diene monomer, styrene-butadiene rubber, fluoro-rubber, various copolymers, and the like.

In addition, the conductive material is not particularly limited, as long as it causes no chemical change in the corresponding battery and has conductivity. The conductive material may be added in an amount of 1 wt %-20 wt % based on the total weight of the solid content in the positive electrode slurry.

Typical examples of the conductive material include: carbon powder, such as carbon black, acetylene black, ketjen black, channel black, furnace black, lamp black or thermal black; graphite powder, such as natural graphite, artificial graphite or graphite having a well-developed crystal structure; conductive fibers, such as carbon fibers or metallic fibers; metal powder, such as carbon fluoride powder, aluminum powder or nickel powder; conductive whisker, such as zinc oxide or potassium titanate; conductive metal oxide, such as titanium oxide; and conductive materials, such as polyphenylene derivatives.

Further, the solvent may include an organic solvent, such as N-methyl-2-pyrrolidone (NMP), and may be used in such an amount that the solvent provides a desired level of viscosity when the positive electrode active material and optionally the binder and the conductive material are incorporated thereto. For example, the solvent may provide a solid content, including the positive electrode active material and optionally the binder and the conductive material, of 10 wt %-60 wt %, preferably 20 wt %-50 wt % in the positive electrode slurry.

(2) Negative Electrode

The negative electrode may be obtained by coating a negative electrode slurry including a negative electrode active material, a binder, a conductive material and a solvent onto a negative electrode current collector, followed by drying and pressing.

The negative electrode current collector generally has a thickness of 3 μm-500 μm. The negative electrode current collector is not particularly limited, as long as it has high conductivity while not causing any chemical change in the corresponding battery. Particular examples of the negative electrode current collector include copper, stainless steel, aluminum, nickel, titanium, baked carbon, or copper or stainless steel surface-treated with carbon, nickel, titanium, silver, aluminum-cadmium alloy, and the like. In addition, similarly to the positive electrode current collector, the negative electrode current collector may have fine surface irregularities formed on the surface thereof to increase the adhesion of a negative electrode active material, and may have various shapes, such as a film, a sheet, a foil, a net, a porous body, a foam or non-woven web body, and the like.

In addition, the negative electrode active material may include at least one selected from the group consisting of a carbonaceous material capable of reversible lithium ion intercalation/deintercalation, metal or alloy of metal with lithium, metal composite oxide, material capable of lithium doping/dedoping, and a transition metal oxide.

The carbonaceous material capable of reversible lithium ion intercalation/deintercalation may include any carbonaceous negative electrode active material used currently in a lithium-ion secondary battery with no particular limitation. Typical examples of the carbonaceous material include crystalline carbon, amorphous carbon or a combination thereof. Particular examples of the crystalline carbon include graphite, such as amorphous, sheet-like, flake-like, spherical or fibrous natural graphite or artificial graphite, and particular examples of the amorphous carbon include soft carbon (low-temperature baked carbon) or hard carbon, mesophase pitch carbide, baked cokes, and the like.

Particular examples of the metal or alloy of metal with lithium include a metal selected from the group consisting of Cu, Ni, Na, K, Rb, Cs, Fr, Be, Mg, Ca, Sr, Si, Sb, Pb, In, Zn, Ba, Ra, Ge, Al and Sn, or an alloy of such a metal with lithium.

The metal composite oxide that may be used is selected from the group consisting of PbO, $PbO_2$, $Pb_2O_3$, $Pb_3O_4$, $Sb_2O_3$, $Sb_2O_4$, $Sb_2O_5$, GeO, $GeO_2$, $Bi_2O_3$, $Bi_2O_4$, $Bi_2O_5$, $Li_xFe_2O_3 (0 \leq x \leq 1)$, $Li_xWO_2 (0 \leq x \leq 1)$, and $Sn_xMe_{1-x}Me'_yO_z$ (wherein Me is Mn, Fe, Pb, Ge; Me' is Al, B, P, Si, element of Group 1, 2 or 3 in the Periodic Table, halogen; and $0 < x \leq 1$; $1 \leq y \leq 3$; and $1 \leq z \leq 8$).

The material capable of lithium doping/dedoping may include Si, $SiO_x$ $(0 < x < 2)$, Si—Y alloy (wherein Y is an element selected from the group consisting of alkali metals, alkaline earth metals, Group 13 elements, Group 14 elements, transition metals, rare earth metals and combinations thereof, except Si), Sn, $SnO_2$, Sn—Y (wherein Y is an element selected from the group consisting of alkali metals, alkaline earth metals, Group 13 elements, Group 14 elements, transition metals, rare earth metals and combinations thereof, except Sn), and the like. At least one of such materials may be used in combination with $SiO_2$. Element Y may be selected from the group consisting of Mg, Ca, Sr, Ba, Ra, Sc, Y, Ti, Zr, Hf, Rf, V, Nb, Ta, db, Cr, Mo, W, Sg, Tc, Re, Bh, Fe, Pb, Ru, Os, Hs, Rh, Ir, Pd, Pt, Cu, Ag, Au, Zn, Cd, B, Al, Ga, Sn, In, Ti, Ge, P, As, Sb, Bi, S, Se, Te, Po, and a combination thereof.

The transition metal oxide may include lithium-containing titanium composite oxide (LTO), vanadium oxide, lithium vanadium oxide, and the like.

The negative electrode active material may be used in an amount of 80 wt %-99 wt % based on the total weight of the solid content in the negative electrode slurry.

The binder is an ingredient which assists binding among a conductive material, an active material and a current collector. In general, the binder may be added in an amount of 1 wt %-30 wt % based on the total weight of the solid content in the negative electrode slurry. Particular examples of the binder include polyvinylidene fluoride, polyvinyl alcohol, carboxymethyl cellulose (CMC), starch, hydroxypropyl cellulose, regenerated cellulose, polyvinyl pyrrolidone, tetrafluoroethylene, polyethylene, polypropylene, ethylene-propylene-diene monomer, styrene-butadiene rubber, fluoro-rubber, various copolymers thereof, and the like.

The conductive material is an ingredient for further improving the conductivity of the negative electrode active material, and may be added in an amount of 1 wt %-20 wt % based on the total weight of the solid content of the negative electrode slurry. The conductive material is not particularly limited, as long as it causes no chemical change in the corresponding battery and has conductivity. Particular examples of the conductive material include: carbon powder, such as carbon black, acetylene black, ketjen black, channel black, furnace black, lamp black or thermal black; graphite powder, such as natural graphite, artificial graphite or graphite having a well-developed crystal structure; conductive fibers, such as carbon fibers or metallic fibers; metal powder, such as carbon fluoride powder, aluminum powder or nickel powder; conductive whisker, such as zinc oxide or potassium titanate; conductive metal oxide, such as titanium oxide; and conductive materials, such as polyphenylene derivatives.

The solvent may include water or an organic solvent, such as NMP, alcohol, and the like, and may be used in such an amount that the solvent provides a desired level of viscosity when the negative electrode active material and optionally the binder and the conductive material are incorporated thereto. For example, the solvent may provide a solid content, including the negative electrode active material and web made of high-melting point glass fibers, polyethylene terephthalate fibers, and the like, may be used with no particular limitation.

There is no particular limitation in the appearance of the lithium secondary battery according to an embodiment of the present disclosure. For example, the lithium secondary battery may have a cylindrical shape using a can, a prismatic shape, a pouch-like shape or a coin-like shape.

Examples will be described more fully hereinafter so that the present disclosure can be understood with ease. The following examples may, however, be embodied in many different forms and should not be construed as limited to the exemplary embodiments set forth therein. Rather, these exemplary embodiments are provided so that the present disclosure will be thorough and complete, and will fully convey the scope of the present disclosure to those skilled in the art.

EXAMPLES

1. Preparation of Non-Aqueous Electrolyte

Mixed solvents were prepared according to the compositions shown in Table 1, and a lithium salt and an additive were introduced thereto to prepare a non-aqueous electrolyte. The content of each of the lithium salt and the additive re also included in Table 1. In addition, the non-aqueous electrolyte according to each of the Examples and Comparative Examples was prepared by further incorporating vinylene carbonate and 1,3-propanesultone (PS) thereto at a concentration of 3 wt % and 0.5 wt %, respectively.

TABLE 1

| | Concentration of lithium salt | | Organic solvent | | | Content of additives (wt %) | |
| | | | Composition of organic solvent (vol %) | | | 1H,1H,5H- | |
| | | | | | Trifluoroethyl methyl | Octafluoropentyl trifluoromethane | Ethylene |
| | LiFSI | LiDFOB | Succinonitrile | Ethyl methyl carbonate | carbonate | sulfonate | sulfite |
|---|---|---|---|---|---|---|---|
| Ex. 1 | 1.3M | — | 100 | — | — | 0.3 | — |
| Comp. Ex. 1 | 1.3M | — | 100 | — | — | 0 | — |
| Comp. Ex. 4 | 1.3M | | 100 | — | — | — | 0.3 |
| Ex. 2 | 0.9M | 0.4M | 93 | 7 | — | 0.1 | — |
| Comp. Ex. 2 | 0.9M | 0.4M | 93 | 7 | — | 0 | — |
| Comp. Ex. 5 | 0.9M | 0.4M | 93 | 7 | — | — | 0.3 |
| Ex. 3 | 2.4M | — | — | 80 | 20 | 0.1 | — |
| Comp. Ex. 3 | 2.4M | — | — | 80 | 20 | 0 | — | optionally the binder and the conductive material, in the negative electrode slurry of 50 wt %-75 wt %, preferably 50 wt %-65 wt %.

(3) Separator

The separator contained in the lithium secondary battery according to the present disclosure may include a conventional porous polymer film, such as a porous polymer film made of a polyolefin-based polymer, including ethylene homopolymer, propylene homopolymer, ethylene/butene copolymer, ethylene/hexene copolymer or ethylene/methacrylate copolymer, and such porous polymer films may be used alone or in the form of a laminate. Otherwise, a conventional porous non-woven web, such as a non-woven

2. Manufacture of Separator

A polyethylene porous substrate (Celgard, PP1615) having a thickness of 16 μm was prepared. A binder resin (PVDF) was added to distilled water and dispersed therein at 25° C. for about 10 minutes to prepare an emulsion binder solution. Next, the binder solution was mixed with alumina particles having an average particle diameter of 0.7 μm and a BET specific surface area of 4 m$^2$/g at a weight ratio of the binder resin to alumina particles of 5:95, and the mixture was dispersed to prepare a slurry for forming a porous coating layer. The slurry for forming a porous coating layer was coated on both surfaces of the porous substrate to obtain a separator. The resultant separator had a total thickness of about 20 μm.

TEST EXAMPLES

Test Example 1: Evaluation of Wettability of Separator with Electrolyte

The wettability of the separator with the non-aqueous electrolyte according to each of Examples 1-3 and Comparative Examples 1-5 was evaluated at 25° C. by using a 2032 coin cell having a diameter of 20 mm and a thickness of 3.2 mm. Particularly, the separator obtained as described above was cut to have a diameter of 18 mm and wetted with the electrolyte according to each of the Examples and Comparative Examples for 24 hours. Then, the separator was interposed between two sheets of stainless steel to assemble a coin cell. The alternating current impedance of the assembled coin cell was measured using an electrochemical impedance spectroscopy (EIS) instrument (Biologic potentiostat), and the film ion conductivity of the separator wetted with the electrolyte was measured. The measured film ion conductivity was divided by the ion conductivity of the electrolyte to calculate the incidence. As used herein, the incidence is an index representing how well the separator is wetted with the electrolyte, and a higher value of incidence shows higher wettability of the separator with the electrolyte. The incidence values of each of the Examples and Comparative Examples are shown in Table 2:

TABLE 2

| | Ex. 1 | Comp. Ex. 1 | Comp. Ex. 4 | Ex. 2 | Comp. Ex. 2 | Comp. Ex. 5 | Ex. 3 | Comp. Ex. 3 |
|---|---|---|---|---|---|---|---|---|
| Incidence of separator (%) | 8.0 | 0.0 | 0.0 | 9.7 | 6.2 | 5.9 | 12.3 | 6.8 |

As seen from the results of Table 2, the nitrile-based electrolytes to which the additive represented by Chemical Formula 1 is added (Examples 1 and 2) show a higher incidence as compared to the nitrile-based electrolytes to which the additive according to the present disclosure is not added (Comparative Examples 1 and 2). Particularly, it can be seen that of the separator is not wetted with the electrolyte when the electrolyte includes 100% of a nitrile-based solvent but does not include an additive according to the present disclosure (Comparative Example 1). It can be also seen that the high-concentration electrolyte to which the additive according to the present disclosure is added (Example 3) shows a higher incidence as compared to the high-concentration electrolyte to which the additive according to the present disclosure is not added (Comparative Example 3). Further, it can be seen that the additive according to the present disclosure shows a higher effect as compared to the additives used in Comparative Examples 4 and 5.

Test Example 2: Evaluation of Surface Tension of Electrolyte

The surface tension at 25° C. of the non-aqueous electrolyte according to each of Example 1, Example 3, Comparative Example 1 and Comparative Examples 3-5 was measured, and the results are shown in Table 3:

TABLE 3

| | Ex. 1 | Comp. Ex. 1 | Comp. Ex. 4 | Ex. 3 | Comp. Ex. 3 | Comp. Ex. 5 |
|---|---|---|---|---|---|---|
| Surface tension (mN/m) | 32 | 41 | 43 | 25 | 34 | 34 |

It can be seen from the results of Table 3 that the nitrile-based electrolyte to which the additive according to the present disclosure is added (Example 1) shows a lower surface tension as compared to the nitrile-based electrolyte to which the additive according to the present disclosure is not introduced (Comparative Example 1). It can be also seen that the high-concentration electrolyte to which the additive according to the present disclosure is added (Example 3) shows a lower surface tension as compared to the high-concentration electrolyte to which the additive according to the present disclosure is not added (Comparative Example 3). Further, it can be seen that the additive according to the present disclosure shows a higher effect as compared to the additives used in Comparative Examples 4 and 5.

Test Example 3: Life Characteristics of Battery $LiNi_{0.5}Co_{0.1}Mn_{0.1}O_2$, carbon black and PVDF were added to a solvent at a weight ratio of 96.8:1.0:2.2, followed by mixing, to prepare a positive electrode slurry composition. The prepared positive electrode slurry composition was applied onto an aluminum current collector having a thickness of 20 μm until the total thickness was 76 μm and then dried at 100° C. for 12 hours to remove the solvent. The resulting structure was pressed by using a roll press to obtain a positive electrode.

In addition, graphite, carbon black and styrene butadiene rubber/carboxymethyl cellulose (SBR:CMC=7:3) were introduced to a solvent at a weight ratio of 95.6:1.0:3.4, followed by mixing, to prepare a negative electrode slurry composition. The prepared negative electrode slurry composition was applied onto a copper current collector having a thickness of 10 μm until the total thickness was 107 μm and then dried at 100° C. for 12 hours to remove the solvent. The resulting structure was pressed by using a roll press to obtain a negative electrode.

The positive electrode and the negative electrode were allowed to face each other, a polyethylene separator having a thickness of 20 μm and a porosity of 45% was interposed between the two electrodes, and then 70 μL of the electrolyte according to each of Examples and Comparative Examples was injected thereto to obtain a mono-cell.

Each battery was charged/discharged to evaluate capacity retention (100 cycles).

Charge condition: constant current (CC)/constant voltage (CV) mode (0.33 C-rate charge, 4.0 V, 0.005 C current cut-off)

Discharge condition: CC mode (0.33 C-rate discharge, 3 V)

The capacity retention was derived by calculating the ratio of the discharge capacity after 100 cycles based on the initial discharge capacity. The results are shown in Table 4:

TABLE 4

|  | Ex. 1 | Comp. Ex. 1 | Comp. Ex. 4 | Ex. 2 | Comp. Ex. 2 | Comp. Ex. 5 | Ex. 3 | Comp. Ex. 5 |
|---|---|---|---|---|---|---|---|---|
| Capacity retention after 100 cycles | 95% | No charging/ discharging | No charging/ discharging | 97% | 67% | 23% | 94% | 55% |

As can be seen from the above results, each of the batteries of Examples 1-3 shows a higher capacity retention compared to the batteries of the Comparative Examples. Each of the batteries according to the Examples of the present disclosure shows a higher capacity retention by virtue of the additive contained in the electrolyte. Therefore, it can be seen that the electrochemical properties of the batteries depend on the presence/absence of the additive.

What is claimed is:

1. A non-aqueous electrolyte for a lithium-ion secondary battery, comprising a lithium salt, an organic solvent and a wettability-improving additive, wherein the wettability-improving additive consists of 1H,1H,5H-Octafluoropentyl trifluoromethane-sulfonate, and is included in an amount of 0.05-3 wt % based on a total weight of the non-aqueous electrolyte, the organic solvent comprises nitrile-based solvent in an amount of 95 wt % or more based on a total amount of the organic solvent, and the nitrile-based solvent comprises succinonitrile.

2. The non-aqueous electrolyte for a lithium ion secondary battery according to claim 1, wherein the lithium salt comprises a $Li^+$ as a cation, and at least one anion selected from the group consisting of $F^-$, $Cl^-$, $Br^-$, $I^-$, $NO_3^-$, $N(CN)_2^-$, $BF_4^-$, $ClO_4^-$, $AlO_4^-$, $AlCl_4^-$, $PF_6^-$, $SbF_6^-$, $AsF_6^-$, $B_{10}Cl_{10}^-$, $BF_2C_2O_4^-$, $BC_4O_8^-$, $PF_4C_2O_4^-$, $PF_2C_4O_8^-$, $(CF_3)_2PF_4^-$, $(CF_3)_3PF_3^-$, $(CF_3)_4PF_2^-$, $(CF_3)_5PF^-$, $(CF_3)_6P^-$, $CF_3SO_3^-$, $C_4F_9SO_3^-$, $CF_3CF_2SO_3^-$, $(CF_3SO_2)_2N^-$, $(FSO_2)_2N^-$, $CF_3CF_2(CF_3)_2CO^-$, $(CF_3SO_2)_2CH^-$, $CH_3SO_3^-$, $CF_3(CF_2)_7SO_3^-$, $CF_3CO_2^-$, $CH_3CO_2^-$, $PO_2F_2^-$, $SCN^-$ and $(CF_3CF_2SO_2)_2N^-$.

3. The non-aqueous electrolyte for a lithium-ion secondary battery according to claim 1, wherein the nitrile-based organic solvent further comprises adiponitrile, acetonitrile, propionitrile, butyronitrile, glutaronitrile, pimelonitrile, suberonitrile, valeronitrile, caprylonitrile, heptane nitrile, cyclopentane carbonitrile, cyclohexane carbonitrile, 2-fluorobenzonitrile, 4-fluorobenzonitrile, difluorobenzonitrile, trifluorobenzonitrile, phenylacetonitrile, 2-fluorophenyl acetonitrile, 4-fluorophenylacetonitrile, or a combination thereof.

4. The non-aqueous electrolyte for a lithium-ion secondary battery according to claim 1, wherein a concentration of the lithium salt is 1.5 M or more.

5. A lithium secondary battery comprising a positive electrode, a negative electrode, a separator and the non-aqueous electrolyte for a lithium-ion secondary battery according to claim 1.

* * * * *